United States Patent [19]

Yokoyama et al.

[11] 4,322,242
[45] Mar. 30, 1982

[54] METHOD OF INCREASING THE YIELD OF HYDROCARBONS FROM PLANTS

[75] Inventors: Henry Yokoyama; Ernest P. Hayman; Wan-Jean Hsu; Stephen M. Poling, all of Pasadena, Calif.

[73] Assignee: The United States of America as represented by the Secretary of Agriculture, Washington, D.C.

[21] Appl. No.: 78,745

[22] Filed: Sep. 25, 1979

Related U.S. Application Data

[62] Division of Ser. No. 891,955, Mar. 31, 1978, Pat. No. 4,204,859.

[51] Int. Cl.³ ............................................. A01N 33/04
[52] U.S. Cl. ............................................. 71/121; 71/98
[58] Field of Search ................................... 71/121, 98

[56] References Cited

U.S. PATENT DOCUMENTS 3,833,350  9/1974  Cooke et al. ..................... 71/121 X
4,159,903  7/1979  Bauman ............................ 71/121 X Primary Examiner—Catherine L. Mills
Attorney, Agent, or Firm—M. Howard Silverstein; David G. McConnell; Margaret A. Connor

[57] ABSTRACT

The accumulation of hydrocarbons in plants which produce the same is enhanced by applying to the plants certain (3,4,5-substituted-phenoxy)-trialkylamines.

1 Claim, No Drawings

METHOD OF INCREASING THE YIELD OF HYDROCARBONS FROM PLANTS

This is a division, of application Ser. No. 891,955 filed Mar. 31, 1978, now U.S. Pat. No. 4,204,859.

BACKGROUND OF THE INVENTION

1. Field of the Invention

This invention relates to and has among its objects the provision of novel processes for increasing the accumulation of hydrocarbons in plants which produce the same. It is a particular object of the invention to increase the amount of rubber in rubber-producing plants. Further objects of the invention will be evident from the following description wherein parts and percentages are by weight unless otherwise specified.

2. Description of the Prior Art

Fossil fuels have been a source of energy for a number of years. Recently, however, it has become apparent that this source of energy is not inexhaustible. Consequently, attention has turned to alternate ways of obtaining energy.

Many plants produce hydrocarbons that can be employed as fuels; rubber, etc. One problem is that such plants do not produce a sufficient quantity of hydrocarbons to make their extraction both economical and feasible. Generally, the hydrocarbons are found throughout the plant tissue, i.e., in the stem, leaves, roots, etc.

SUMMARY OF THE INVENTION

A principle object of the invention is to obviate the problem outlined above. The invention provides means whereby the accumulation of hydrocarbons in plants producing the same is increased substantially.

Basically, the objects of the invention are attained by applying to the plant any of the following compounds:

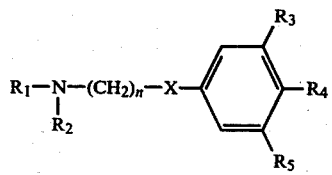

wherein:
X is either oxygen or sulfur,
$R_1$ and $R_2$ are lower alkyl containing from 1 to 3 carbon atoms,
$R_3$, $R_4$, and $R_5$ are independently hydrogen, chlorine, bromine, iodine, lower alkyl containing from 1 to 5 carbon atoms, lower alkoxy containing from 1 to 5 carbon atoms or condensed mono- and polycyclic aromatic ring systems, and
n is an integer from 1 to 3; and wherein:
if $R_5$ is hydrogen, $R_3$ and $R_4$ must be other than hydrogen; and wherein:
if $R_3$ and $R_5$ are hydrogen, $R_4$ must be a branched-chain alkyl group containing from 3 to 5 carbon atoms or an alkoxy group containing a branched-chain alkyl group of 3 to 5 carbon atoms; and wherein:
if $R_4$ is hydrogen, $R_3$ and $R_5$ must be branched-chain alkyl groups containing from 3 to 5 carbon atoms or alkoxy group containing branched-chain alkyl groups of 3 to 5 carbon atoms or chlorine, bromine, or iodine.

The primary advantage of the invention is that the yield of hydrocarbons in plants treated by the instant process is increased from 200 to 600% over non-treated plants.

Another advantage of the compounds of the invention is that they do not cause damage to the plant foliage, nor do they hinder the growth of the plant. Furthermore, the process of the invention will result in an increase of hydrocarbons whether the instant compounds are applied to the plants during growth periods or during dormant periods.

DESCRIPTION OF THE PREFERRED EMBODIMENTS

As mentioned above the benefits of the invention are obtained by applying to the plant to be treated any of the aforementioned compounds. Examples, by way of illustration and not limitation, of compounds that can be used in the process of the invention are:

A. (3,4,5-Substituted phenoxy) alkyldialkylamines wherein the 3,4, and 5-substituents are independently either chloro, bromo, iodo, methoxy, ethoxy, propoxy, butoxy, pentoxy, methyl, ethyl, propyl, butyl, or pentyl, and wherein the alkyl and dialkyl group are independently either methyl, ethyl, or propyl.

B. (4-Substituted phenoxy) alkyldialkylamines wherein the 4-substituent is either iso-propoxy, iso-butoxy, isopentoxy, t-butoxy, t-pentoxy, iso-propyl, iso-butyl, iso-pentyl, t-butyl, or t-pentyl, and wherein the alkyl and dialkyl groups are the same as those in A.

C. (3,5-Substituted phenoxy) alkyldialkylamines wherein the 3,5-substituents are independently iso-propoxy, iso-butoxy, iso-pentoxy, t-butoxy, t-pentoxy, iso-propyl, iso-butyl, iso-pentyl, t-butyl, t-pentyl, chlorine, bromine, or iodine, and wherein the alkyl and dialkyl groups are the same as those in A.

D. (Naphthoxy) alkyldialkylamines wherein the alkyl and dialkyl groups are the same as those in A.

E. Compounds of A through D above wherein sulfur is substituted for oxygen.

For the method disclosed in this invention, the preferred compounds are those wherein n is 1, X is oxygen, the phenoxy substituents are 3,4-dichloro, and the dialkyl groups are diethyl.

Various acid addition salts of the above compounds are readily available. For example, by adding acid to the compounds of the invention, the following acid addition salts are formed

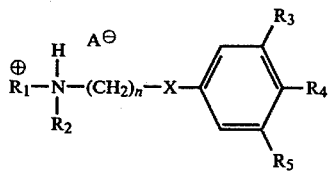

wherein:
X is either oxygen or sulfur
$R_1$ and $R_2$ are lower alkyl containing from 1 to 3 carbon atoms,
$R_3$, $R_4$, and $R_5$ are independently hydrogen, chlorine, bromine, iodine, lower alkyl containing from 1 to 5 carbon atoms, lower alkoxy containing from 1 to 5 carbon atoms, or condensed mono- and polycyclic aromatic ring systems, and n is an integer from 1 to 3; and wherein:

if $R_S$ is hydrogen, $R_3$ and $R_4$ must be other than hydrogen; and wherein:

if $R_3$ and $R_5$ are hydrogen, $R_4$ must be a branched-chain alkyl group containing from 3 to 5 carbon atoms or an alkoxy group containing a branched-chain alkyl group of 3 to 5 carbon atoms; and wherein:

if $R_4$ is hydrogen, $R_3$ and $R_5$ must be branched-chain alkyl groups containing from 3 to 5 carbon atoms or alkoxy group containing branched-chain alkyl groups of 3 to 5 carbon atoms, or chlorine, bromine, or iodine; and wherein:

A is the anion derived from the acid added to the amine to form a salt.

The compounds of the invention are applied to the entire plant including the branches, leaves, etc., in an amount sufficient to increase the yield of hydrocarbons therefrom. It is convenient and desirable, though not necessary, to mix the compounds with a suitable carrier prior to application to the plant. For example, the compounds may be mixed with carriers to form solutions, emulsions, wettable powder dispersions, dust formulations and the like.

Solvents which may be used as a carrier for the compounds of the invention should be volatile and not interfere with either the plant tissue or the compounds of the invention. Examples of suitable solvents, by way of illustration and not limitation, are acetone, ethyl ether, isopropanol, and the like. Generally, the concentration of the compound in the solvent should be about 300 to 10,000 ppm (parts per million). The concentration depends somewhat on the type of plant; for perennial plants approximately 2000–5000 ppm is used, for annuals, lower concentrations, 300–1000 ppm, are employed.

It is also possible to employ the compounds of the invention by forming an emulsion. By dissolving the compounds in a water-immiscible solvent and adding an emulsifying agent, an emulsifiable concentrate is produced. When water is added to this concentrate, an emulsion is obtained, which may be applied to the plant to be treated.

The compounds of the invention may be used in the form of powders prepared by mixing them with conventional excipients, such as surfactants, fillers, and the like.

For dust formulations, the compounds used in the process of the invention may be absorbed onto solid carriers. Suitable carriers are, for example, vermiculite, attaclay, talc, and the like.

The compounds of the invention may be applied to the plant in any convenient manner suggested to those skilled in the art. For example, the compound dissolved in a suitable solvent can be sprayed onto the branches and leaves of the plants. Other application techniques and equipment known to the skilled artisan may be employed.

Preferably, the plants are treated during periods of stress or dormancy to maximize the yield of hydrocarbons. However, good results are obtained also if the compounds of the invention are applied to the plants during periods of vegetative growth.

It is within the compass of the invention to use the instant compounds in conjunction with certain alcohols or thiols of the structure

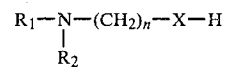

wherein:

X is either oxygen or sulfur $R_1$ and $R_2$ are lower alkyl containing from 1 to 3 carbon atoms, and n is an integer from 1 to 3.

The above alcohols and thiols by themselves are ineffective in increasing the yield of hydrocarbons in plants. However, when they are employed in conjunction with the aforementioned compounds, a synergistic effect is obtained wherein the activity of the latter compounds in accordance with the invention is enhanced.

To facilitate application of the compounds of the invention to the plants when using water as a medium, it is permissible, though not mandatory, to add a wetting agent to the aqueous dispersion. Any commercial wetting agent may be employed; for example, one may add ORTHO X-77 (a mixture of fatty acids, fatty alcohols, and isopropanol made by Chevron Chemical Company), Sweep 4F (chlorothalonil from Diamond Shamrock Company), and so forth.

The method of the invention will enhance the accumulation of hydrocarbons in any plant that produces such hydrocarbons. One important use of the present method is to increase the yield of rubber from plants such as guayule (*Parthenium argentatum* Gray), Hevea (*Hevea brasiliensis*, Muell.), *Euphorbia tirucalli, Tararacum kok-saghyz Rodin, Euphorbia dendroides,* and the like. The method of the invention is useful in increasing the accumulation of hydrocarbons in other plants, such as Euphorbia lathyrus, *Euphorbia marlothii, Asclepias cursavica, Cryptostegia grandiflora, Eucalyptus glubulus, Jatropha curcas, Monadenium rhizophorum, Sarcostemma viminale, Synadenium grantii, Achcas sapota, Asclepias sp., Euphorbia coerulescens, Euphorbia trigona,* and so forth.

Hydrocarbons are any of a large class of organic compounds containing only carbon and hydrogen, comprising paraffins, olefins, acetylenic compounds, aliphatic compounds, alicyclic compounds, aromatic compounds, etc.

It should be noted that the compounds of the invention are not detrimental to the plants to which they are applied. The treated plants continue to grow at the same rate as untreated plants with no damage to the plant itself.

The compounds of the invention may be prepared according to known procedures as outlined by Scheutz and Baldwin in the *Journal of the American Chemical Society,* Vol. 80, p. 162 (1958). The general reaction scheme may be outlined as follows:

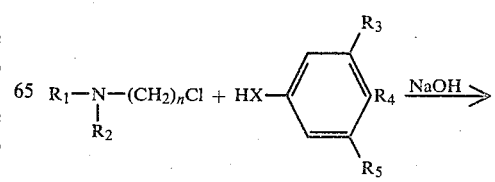

-continued

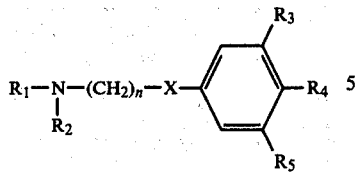

The activity of the compounds of the invention are unusual and unexpected because it is not shared by other closely-related compounds. For example, the following compounds are not effective in the process of the invention:

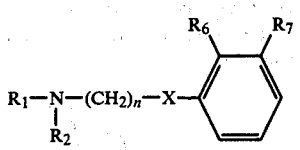

wherein:
X is either oxygen or sulfur
$R_1$ and $R_2$ are lower alkyl containing from 1 to 3 carbon atoms,
$R_6$ and $R_7$ are independently hydrogen, chlorine, bromine, iodine, lower alkyl containing from 1 to 5 carbon atoms, lower alkoxy containing from 1 to 5 carbon atoms, or condensed mono- and polycyclic aromatic ring systems, and
n is an integer from 1 to 3.

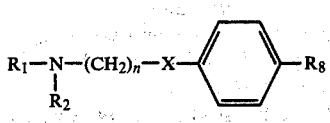

wherein:
X is either oxygen or sulfur,
$R_1$ and $R_2$ are lower alkyl containing from 1 to 3 carbon atoms,
$R_8$ is hydrogen, chlorine, bromine, iodine, a straight-chain alkyl group containing 1 to 5 carbon atoms, or a lower alkoxy group containing a straight-chain alkyl group of 1 to 5 carbon atoms, and
n is an integer from 1 to 3.

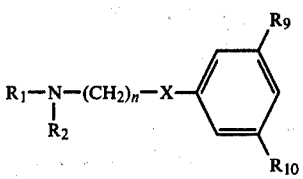

wherein:
X is either oxygen or sulfur,
$R_1$ and $R_2$ are lower alkyl containing from 1 to 3 carbon atoms,
$R_9$ and $R_{10}$ are hydrogen, straight-chain alkyl groups containing 1 to 5 carbon atoms, or lower alkoxy groups containing straight-chain alkyl groups of 1 to 5 carbon atoms, and
n is an integer from 1 to 3.

EXAMPLES

The invention is further demonstrated by the following illustrative examples.

EXAMPLE 1

The compound 2-(3,4-dichlorophenoxy)-triethylamine (DTA) was synthesized from 2-diethylaminoethyl chloride and 3,4-dichlorophenol according to the procedure of R. D. Scheutz and R. A. Baldwin as mentioned hereinabove.

Selected strains of greenhouse-grown seedlings of guayule plant, Parthenium argentatum Gray (10 cm. high, 4 months old) were obtained from the Los Angeles County Arboretum, Los Angeles, Calif.

An aqueous dispersion containing 5000 ppm (parts per million) of 2-(3,4-dichlorophenoxy)-triethylamine (DTA) and 125 ppm ORTHO X-77 was prepared. Four guayule plants, strain 235, were selected at random from the above-mentioned collection. The plants were sprayed with the aqueous dispersion prepared above and allowed to grow in a green house. After 3 weeks from the date of treatment all of the plants, each in the state of vigorous vegetative growth, were harvested.

The amount of hydrocarbons in the form of rubber, i.e., cis-1,4-polyisoprene, in the plants was determined as follows: Dead twigs and branches, remnants of flower penduncles and leaves were removed from the stems. The stem and root (swollen crown) portions were dried rapidly at 65° C., comminuted, and ground in a hammermill. The ground material was extracted sequentially in a Polytron apparatus (a device for disintegrating the cells) with first water, then acetone, and then methylene chloride. The rubber was found in the methylene chloride extract, which was evaporated to give a solid residue. The solid was dissolved in methylene chloride and precipitated by addition of acetone. The precipitate was collected by filtration and dried in vacuo to a constant weight. The solid residue was identified as cis-1,4-polyisoprene by Nuclear Magnetic Resonance (NMR) spectroscopy on carbon 13 ($^{13}C$).

The above procedure was repeated on several strains of guayule plant, namely 245 and 244.

Similar runs were made using an aqueous dispersion containing 5000 ppm of DTA, 5000 of 2-diethylaminoethanol (DA), and 125 ppm of ORTHO X-77.

The following controls were also run: Plants were either not sprayed or sprayed with aqueous dispersions of either 2-diethylaminoethanol (5000 ppm) or ORTHO X-77 (125 ppm).

The results are summarized in the following table. Each result represents the average of the values from four plants.

| Strain of guayule plant | Rubber content (mg/g dry weight of plant) | | | | | |
|---|---|---|---|---|---|---|
| | Treatment of invention | | Controls | | | |
| | DTA, DA, X-77 | DTA, X-77 | DA, X-77 | DA | X-77 | None |
| 235 | 32.3 | 26.7 | 9.5 | 9.6 | 9.2 | 8.9 |
| 245 | 41.0 | 34.2 | 15.0 | 15.4 | 14.6 | 15.2 |
| 244 | 28.0 | 22.5 | 13.0 | 12.9 | 13.4 | 12.6 |

EXAMPLE 2

The procedure outlined in Example 1 was followed. Field-grown guayule plants (8 months old) were employed in place of the greenhouse-grown plants of Example 1. In addition, 500 ppm of Sweep 4F was substituted for the ORTHO X-77.

The results are tabularized below. Each number represents an average for five plants.

| Strain of guayule plant | Rubber content (mg/g dry weight of plant) | | | | | |
|---|---|---|---|---|---|---|
| | Treatment of invention | | Controls | | | |
| | DTA, DA, X-77 | DTA, X-77 | DA, X-77 | DA | X-77 | None |
| 233 | 24.0 | 19.2 | 8.2 | 8.6 | 7.9 | 8.4 |
| 240 | 36.5 | 30.4 | 10.0 | 10.4 | 9.6 | 10.8 |
| 240* | 66 | 60.2 | 11 | 10.6 | 11.2 | 10.6 |

*The entire plant was harvested 3 weeks after treatment and maintained barerooted in complete Hoagland's nutrient solution for one week. The result is for one plant only.

EXAMPLE 3

The procedure described in Example 1 was employed with the following changes: Cuttings with attached foliage were used instead of whole plants and were maintained in complete Hoagland's nutrient solution with added sodium acetate for ten days.

The procedure was repeated using, in place of DTA, 2-(4-chlorophenoxy)-triethylamine (CTA), 2-(4-ethylphenoxy)-triethylamine (ETA), and 2-(2,4-dichlorophenoxy)-triethylamine (DPTA). The latter compounds are not in accordance with the invention but are provided for purposes of comparison.

The results are summarized below; each number represents an average value for three cuttings:

| Treatment | Rubber content (mg/g dry weight of cutting) |
|---|---|
| DTA | 229 |
| CTA* | 70 |
| ETA* | 82 |
| DPTA* | 87 |
| Control, water + X-77* | 57 |

*Not in accordance with the invention.

EXAMPLE 4

The procedure described in Example 3 was followed using the following compounds: 2-(3,5-isopropylphenoxy)-triethylamine (ITA), 2-(3-methyl-4-chlorophenoxy)-triethylamine (MCTA), 2-(4-t-butylphenoxy)-triethylamine (BTA), 2-(3,4,5-trichlorophenoxy)-triethylamine (TCTA), 2-(2-naphthoxy)-triethylamine (NTA), and 2-(3,5-dichlorophenoxy)-triethylamine (DCPTA). Strain 593 of guayule plant was treated.

Similar runs were made using aqueous dispersions containing 5000 ppm of one of the above compounds, 5000 ppm of DA, and 125 ppm of ORTHO X-77.

The following controls were also run: Cuttings were either not sprayed or sprayed with aqueous dispersions of either DA (5000 ppm) or ORTHO X-77 (125 ppm).

The results are tabularized below; each result represents average value for three cuttings:

| Compound | Rubber content (mg/g dry weight of cutting) | | | | | |
|---|---|---|---|---|---|---|
| | Treatment | | Control | | | |
| | Compound + DA + X-77 | Compound + X-77 | DA + X-77 | DA | X-77 | None |
| ITA | 123 | 116 | 56 | 52 | 58 | 51 |
| MCTA | 108 | 96 | 46 | 51 | 43 | 47 |
| BTA | 102 | 91 | 49 | 54 | 46 | 42 |
| TCTA | 92 | 83 | 36 | 36 | 40 | 34 |
| NTA | 86 | 74 | 38 | 40 | 41 | 37 |
| DCPTA | 76 | 63 | 37 | 39 | 36 | 39 |

Having thus described our invention, we claim:

1. The process for increasing the accumulation of rubber hydrocarbons in a plant that produces the same, which comprises applying to the plant an effective amount of a mixture, said mixture comprising a compound of the structure

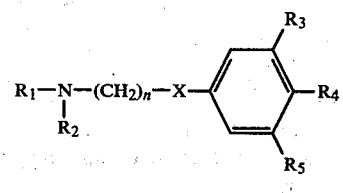

wherein:
X is either oxygen or sulfur,
$R_1$ and $R_2$ are lower alkyl containing from 1 to 3 carbon atoms,
$R_3$, $R_4$ and $R_5$ are independently hydrogen, chlorine, bromine, iodine, lower alkyl containing from 1 to 5 carbon atoms, lower alkoxy containing from 1 to 5 carbon atoms, or condensed mono- and polycyclic aromatic ring systems, and
n is an integer from 1 to 3; and wherein:
if $R_5$ is hydrogen, $R_3$ and $R_4$ must be other than hydrogen; and wherein:
if $R_3$ and $R_5$ are hydrogen, $R_4$ must be a branched-chain alkyl group containing from 3 to 5 carbon atoms or an alkoxy group containing a branched-chain alkyl group of 3 to 5 carbon atoms; and wherein:
if $R_4$ is hydrogen, $R_3$ and $R_5$ must be branched-chain alkyl groups containing from 3 to 5 carbon atoms or alkoxy groups containing branched-chain alkyl groups of 3 to 5 carbon atoms or chlorine, bromine, or iodine;
mixed together with a compound of the structure

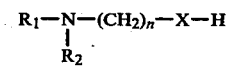

wherein:
X is either oxygen or sulfur,
$R_1$ and $R_2$ are lower alkyl containing from 1 to 3 carbon atoms, and
n is an integer from 1 to 3.

* * * * *